United States Patent [19]
Alba

[11] Patent Number: 5,121,629
[45] Date of Patent: Jun. 16, 1992

[54] METHOD AND APPARATUS FOR DETERMINING PARTICLE SIZE DISTRIBUTION AND CONCENTRATION IN A SUSPENSION USING ULTRASONICS

[75] Inventor: Felix Alba, Murray, Utah

[73] Assignee: E. I. Du Pont de Nemours and Company, Wilmington, Del.

[21] Appl. No.: 436,153

[22] Filed: Nov. 13, 1989

[51] Int. Cl.$^5$ .............................................. G01N 15/02
[52] U.S. Cl. .................................. 73/61.41; 73/602; 73/865.5
[58] Field of Search ................ 73/61 R, 61.1 R, 599, 73/602, 628, 865.5, 19.03

[56] References Cited

U.S. PATENT DOCUMENTS

| | | | |
|---|---|---|---|
| 3,779,070 | 12/1973 | Cushman et al. | 73/628 X |
| 4,412,451 | 11/1983 | Uusitalo et al. | 73/61 R |
| 4,706,509 | 11/1987 | Riebel | 73/61 R |

Primary Examiner—Hezron E. Williams
Assistant Examiner—Rose M. Finley

[57] ABSTRACT

The present invention relates to method and apparatus for determining the size distribution and concentration of particles in suspensions, emulsions or aerosols utilizing ultrasonic excitation. The invention is applicable over a wide range of particle sizes (0.01 to 1,000 microns) and concentrations (0.1% to 70% by volume). The present invention is particularly useful for industrial on-line measurement and control of highly concentrated slurries. The method comprises the steps of directing ultrasonic waves through the suspension at selected discrete frequencies over a selected frequency range and measuring the attenuation of the ultrasonic waves passing through the suspension for each of the selected discrete frequencies to thereby obtain a measured attenuation spectrum for the suspension over the selected frequency range. The method further comprises the steps of calculating a set of attenuation spectra for the ultrasonic waves passing through the suspension over the selected frequency range using a set of original values of particle size distribution and concentration and comparing the measured attenuation spectrum with the calculated attenuation spectra to derive an approximate match between at least one of the calculated spectra and the measured spectrum within a selected error range. The method further comprises the step of selecting the size distribution and concentration of the particles used to calculate the attenuation spectra to thereby derive a new set of values of particle size distribution and concentration corresponding to the measured attenuation spectrum.

13 Claims, 7 Drawing Sheets

METHOD AND APPARATUS FOR DETERMINING PARTICLE SIZE DISTRIBUTION AND CONCENTRATION IN A SUSPENSION USING ULTRASONICS Attached hereto are microfiche containing 63 frames of programs which can be employed in the described embodiments and in other embodiments. These microfiche are hereby incorporated by reference.

This invention relates to a method and apparatus for determining the particle size distribution and concentration of particles in suspensions, emulsions or aerosols utilizing ultrasonic excitation. The present invention is applicable to a suspension of solid, liquid or gaseous particles in any type of suspending fluid medium, and it is understood that the term "suspension" as used herein is intended to include all such media.

Various apparatus and methods for approximating particle size distribution and concentration in a suspending medium utilizing ultrasonic excitation are known in the prior art. In one such known method as disclosed in U.S. Pat. No. 4,706,509—Riebel, issued Nov. 17, 1987, a suspension of particles in a suspending medium is excited by ultrasonic waves and the attenuation of the ultrasonic waves in passing through the suspension is measured. Attenuation measurements are made at a plurality of frequencies within a selected frequency range based on a division of the dimensional spectrum of the particles into a plurality of dimensional intervals. The measured absorptions at each frequency are represented in the form of a sum of the products of the absorption coefficients which are specific to the frequency and dimensional intervals with the unknown particle concentrations, to form a linear equation which is solved in a known manner with respect to the unknown concentrations. The range of frequencies used is preferably selected such that the wavelength of the highest frequency is about equal to or smaller than the smallest particles to be measured and the wavelength of the lowest frequency is about equal to or larger than the largest particles to be measured.

In the method just described, the range of particle sizes to be measured should preferably be known in advance and the number of frequency intervals should be selected to be equal to the number of particle size dimensional intervals. The method is based on the assumption that the measurements can be represented in the form of a set of linear equations involving unknown quantities which can be solved by known techniques.

The accuracy of the method just described is limited to a relatively narrow range of conditions in which certain general parameters are already known in advance and where simple superposition and linear techniques may suffice to give results deemed acceptable under such limited circumstances. The method does not take into account the very substantial non-linearities which exist in systems wherein measurements must be made over an extended range of conditions, many of which can not be determined in advance. As a result, the method is further generally limited to low concentrations, typically less than 10% to 15% by volume, and relatively large particle size distributions where the minimum particle size is in excess of 5 to 10 microns.

In an apparatus employing another method utilizing ultrasonic excitation as disclosed in U.S. Pat. No. 3,779,070—Cushman et al., issued Dec. 18, 1973, two beams of ultrasonic energy of different frequencies are directed through a slurry and the attenuation of each beam is separately measured. The beam frequencies are chosen so that the attenuation of each beam is a different function of the percent solids by volume of the slurry, the geometric mean particle diameter, the standard deviation of the distribution of the particles, and the size of the largest particles in the slurry. The monitoring of these parameters by the disclosed apparatus is effected by making in each case a single instantaneous measurement of the attenuation in each of the single frequency beams. These measurements are based on substantial accumulations of empirically derived data applicable to a particular field, namely mining, in which particulate containing slurries of known ores are used in recovery processes. The invention only provides one point in the cumulative size distribution (the percentage of material passing a reference mesh) and, for its proper operation, a correlation between the mean size and the spread of the distribution must be valid. Besides, it only works for the typically coarse and broad distributions produced by mining ore grinding operations (mean sizes over 20 $\mu$m). The disclosed apparatus and its related methodology are thus not suitable for widespread application.

Other apparatus and or methods have been described in the prior-art for sensing, identifying or detecting particulates using ultrasonics. Uusitalo et al in U.S. Pat. No. 4,412,451, issued Nov. 1, 1983 extended the method previously described in U.S. Pat. No. 3,779,070 by simultaneously measuring attenuation and scattering at a certain angle. They claimed more accurate measurements could be achieved but, similarly to the method developed by Cushman, only the average size could be determined.

In addition, the following patents address particle analysis: U.S. Pat. No. 3,774,717 issued Nov. 27, 1973; U.S. Pat. No. 3,802,271 issued Apr. 9, 1974; U.S. Pat. No. 3,921,622 issued Nov. 25, 1975; U.S. Pat. No. 4,015,464 issued Apr. 5, 1977; U.S. Pat. No. 4,112,773 issued Sep. 12, 1978; U.S. Pat. No. 4,339,944 issued Jul. 20, 1982; U.S. Pat. No. 4,381,674 issued May 3, 1983; U.S. Pat. No. 4,412,451 issued Nov. 1, 1983; U.S. Pat. No. 4,527,420 issued Jul. 9, 1985 and U.S. Pat. No. 4,739,662 issued Apr. 26, 1988. These patents describe methods and/or apparatus which can only work for extremely low particle concentrations (at the contamination levels) and/or have similar limitations of previously cited patents.

There are three main difficulties in developing a method and apparatus for measuring particle size distribution and concentration using ultrasonics which is to be workable in the general case, i.e. any type of suspension (solid in liquid, liquid in liquid, solid in gas or liquid in gas), low and high concentration, broad range of particle mean size (submicron as well as coarse sizes up to 1,000 micrometers), and wide range of size distribution spreads (very narrow distributions as well as very broad ones). They are:

1) Sound propagation phenomena in particulates have to be mathematically described and coded in computer software. This involves solving the wave equations which model the interaction between sound and the suspended particles and calculating the attenuation spectrum for each particle size distribution, concentration, chemical composition of the phases in the suspension and frequency of the wave. Furthermore, multiple-scattering phenomena, dominant for high particle concentrations, are difficult to mathematically describe and, finally, the resulting equations require non-standard sophisticated numerical procedures for their solution to be accurately obtained in a computer of modest computing power.

2) Once the relationship between size distribution, concentration, attenuation and frequency has been quantified, the determination of the size distribution and concentration of an unknown sample is accomplished by measuring the attenuation of the wave as a function of frequency and "looking backwards" to identify the size distribution and concentration which produced the measured attenuation spectrum. This is a very delicate problem, the solution of which has motivated the creation of a separate realm of mathematics called Inversion Mathematics. The inherent non-uniqueness and instability of the equations to be inverted make any attempt of inverting them using actual spectrum data (with measurement errors and noise), in a digital computer (with round-off errors), an extremely difficult task. Direct matrix inversion techniques would amplify normal minute variations on the measured spectrum to the point that the solution would have no physical meaning at all (e.g. negative size fractions and/or concentration) or, for some slightly more elaborated techniques which attempt to overcome the instability, the solution is artificially distorted.

3) The accurate measurement of the attenuation due only to the suspension requires the devising of a measuring technique which nulls out the intrinsic response of the transducers, transmitting and receiving electronics and wiring as well as the loading effect that the suspension imposes on the transducers which, in turn, reflect on the final measurement of the attenuation of the wave. Furthermore, low attenuations can not be measured accurately and high attenuations leave undetectable signals (low signal/noise ratio) on the receiver. Particularly, in order for the method to be able to measure particle sizes below a micron, the capacity of accurately measuring very low and very high attenuations is paramount and, in this case, that can only be accomplished when all those mentioned artifacts are properly compensated for. This is one the reasons why several attempts in the prior art to experimentally test mathematical models for ultrasonic attenuation have shown poor agreement between predicted and measured spectra.

The prior art methods have thus relied upon simplifications such as assumptions of linearity, in which case the method can have only approximate accuracy within a limited range, and/or have been limited in their applications to known systems where empirically developed data are used to assist in deriving approximations of the parameters being measured, again with only limited applications being possible.

SUMMARY OF THE INVENTION

The present invention provides a method for determining the particle size distribution and concentration in a suspension which is capable of more general application. In one embodiment thereof, a sample of a suspension is excited with ultrasonic energy over a range of separate and discrete frequencies, the attenuation at each frequency is measured to derive a measured attenuation spectrum for the sample, the attenuation spectrum for any size distribution and concentration in an ample range is calculated (by means of a fundamental mathematical model), and the calculated and measured attenuation spectra are compared to determine the actual particle size distribution and concentration of the sample. In accordance with a preferred embodiment, a number of separate solution techniques to the mathematical problem for calculating particle size distribution and concentration are stored, each of the inversion techniques having known limitations as a general case solution but being preferred for a particular range of parameters within the general case. From the measured attenuation spectrum, qualitative features of the spectrum are recognized to obtain a first approximation of the sample size distribution and concentration. Secondly, a proper numerical technique or sequence of numerical techniques is selected to accurately determine the actual size distribution and concentration. The invention employs a combination of numerical non-linear estimation tools, pattern recognition techniques and heuristic knowledge stored in the computer.

The invention relies on the accurate measurement of the attenuation spectrum; and specific techniques to compensate for any artifacts due to the electronic hardware and transducers are integral part of the method so a good agreement between the measured and predicted spectra can be obtained. The invention also relies on exciting the suspension with an ultrasonic wave as close as possible to the ideal case of a plane-wave regime; and the employment of transducers specifically designed to avoid the transmission of "edge waves" is a part of one embodiment of the invention so a good accuracy of the mathematical model, in its ability to predict the attenuation spectrum, can be assured.

An automatic feedback control of the spacing between transmitter and receiver transducers increases the signal/noise ratio for the spectral measurements. The general solution of the ultrasound wave equations combined with the referred measurement techniques, make it possible to measure sizes smaller than a micron and concentrations higher than 15% by volume. The invention is thus capable of use for general applications where the particle size distribution and concentration of a sample are both initially totally unknown.

In a further embodiment, certain selected portions of the calculation of the attenuation spectra are performed off line in advance and stored in an addressable matrix in the on-line computer and used in the performance of the on-line calculations of the attenuation spectra. This permits the on-line portion of the calculations to be made in a relatively short time consistent with the requirements for on-line, real-time process control and with the need for computing hardware of modest complexity and cost compatible with such process control systems.

DETAILED DESCRIPTION OF THE INVENTION

Figure 1:
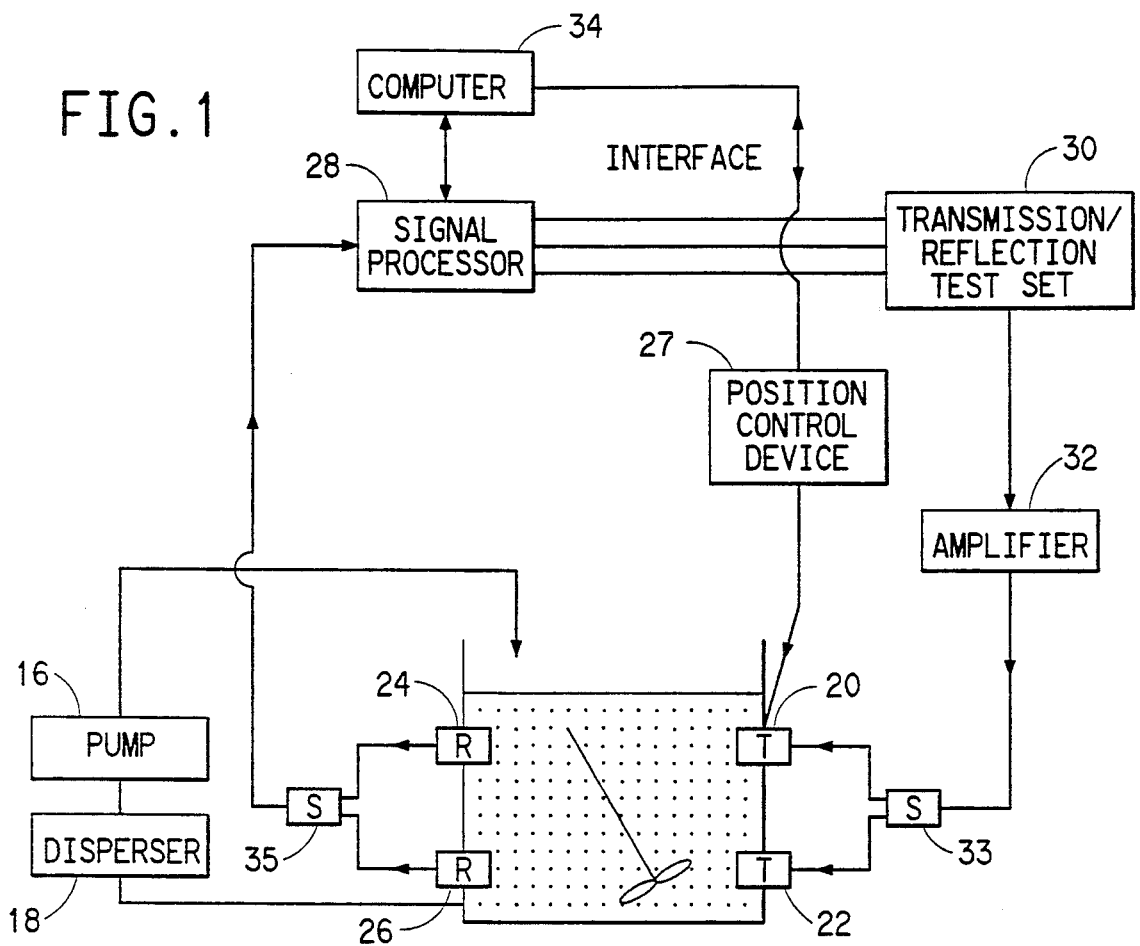
FIG. 1 is a block diagram of a system for practicing the method of the present invention in accordance with one embodiment thereof.

Referring to the block diagram of FIG. 1, the system includes an ultrasound absorption chamber 10 which contains a suspension 12 which is to be analyzed. The suspension 12 consists of a dispersion of particles of unknown size distribution and concentration suspended in a suspending medium. An agitator 14 may be and is preferably employed to maintain the homogeneity of the suspension 12. In addition, the suspension 12 may be circulated by means of a pump 16 through an ultrasonic disperser 18 to prevent agglomeration of fine particles. The dispersion and agitation should be selected to be sufficient to maintain homogeneity and dispersion of the particles but should not be overly vigorous as this will cause introduction of air bubbles which will interfere with the measurements to be made.

Two very high dynamic range, broad-band ultrasonic transmitter transducers 20 and 22 utilizing piezoelectric copolymer films are provided to cover a wide frequency range of about 0.5 Mhz to 100 Mhz. The transducers 20 and 22 are designed to avoid the transmission of "edge waves", i.e. to transmit an acoustical wave as close as possible to the ideal plane-wave regime assumed by the mathematics employed in this invention. A pair of receiver transducers 24 and 26 are mounted opposite the transmitter transducers 20 and 22 to receive the ultrasonic waves transmitted by transducers 20 and 22 after the attenuation of such waves in the suspension 12. Different embodiments for the invention could utilize different ultrasonic transmission/reception arrangements like pulse-echo, broad-band transmission/detection, tone-burst transmission/detection, several transducers, harmonic excitation, and the like. Similarly, the number of transducers could be increased or reduced, depending on the bandwidth and dynamic range of the transducers and frequency range of interest.

The distance between the transmitter transducers 20 and 22 and the receiver transducers 24 and 26 is made adjustable in fine increments from a position of very close proximity where the separation distance is almost zero to a full separation of about 4 inches or so. This allows measurement of a wide range of attenuations from as low as a few dB/inch to as high as more than 1,000 dB/inch, which is a range expected to be found in suspensions excited over such a wide frequency band. The transmitting and receiving faces of the transmitter and receiver transducers are maintained in close parallel relation to each other as the distance between them is adjusted. For best results, a parallelism between the faces of within at least 2.5 $\mu$m/cm is maintained. The distance between the transmitter transducers 20 and 22 and the receiver transducers is maintained by a position control device 27 which may be and preferably is under computer control.

A signal processor 28 is provided to perform the functions of signal generation, signal reception and measurement of the attenuation spectrum. In one embodiment of the invention, a Hewlett-Packard Network Analyzer (HP-8753B) was employed as the signal processor 28. Signal generation over a wide frequency range preferably from about 0.5 Mhz to about 100 Mhz at selected discrete frequencies is provided. The system preferably uses the heterodyne principle of detection in which all frequencies in the measurement range are transformed to a single selected and preferably low frequency for measurement. This provides a high dynamic range (over 100 dB) and permits accurate measurement of attenuation as a function of frequency. A transmission/reflection test set 30 is provided to measure simultaneously the transmitted as well as reflected waves for each selected measurement frequency. In one embodiment, a Hewlett-Packard test set HP-85044A was employed as the test set 30.

A power amplifier 32 is connected between a signal generating RF transmitter of signal processor 28 and the transmitter transducers 20 and 22 to amplify the signal from the processor 28 through the test set 30 and compensate for the transducer insertion loss to increase further the dynamic range of the system. In one embodiment of the invention, an amplifier model ENI 3100LA was used as the amplifier 32. Each transmitter/receiver transducer pair operates alternatively by means of computer controlled microwave switches.

The system is controlled by a computer 34 in a manner later to be described in detail. In one embodiment, a Compaq computer model 386/20 running at a 20 Mhz clock rate was employed as the computer 34. This computer was based on the Intel 80386 processor plus the 80387 mathematical coprocessor and had 1 Mbyte of main memory and a 60 Mbyte hard disk. It is to be understood that any other computer with similar computation power could be utilized to perform the same functions.

The system of FIG. 1 operates to transmit ultrasonic waves at selected, discrete frequencies within the 0.5 Mhz to 100 Mhz range from the transmitter transducers 20 and 22 through the suspension 12 for reception by the receiver transducers 24 and 26 and the measurement of the attenuation in the suspension 12 at each such selected frequency. In order to null out the effects on the signal of the inherent characteristics of the transmitter and receiver transducers and the associated wiring and other apparatus used in the system, attenuation measurements are taken at each selected discrete measurement frequency with the transmitter and receiver transducers at different distances apart and the results ratioed to remove such system constants. This technique assures that the measured attenuation accurately represents the attenuation due only to the suspension and not to the intrinsic response of transducers and electronics. Two important benefits are obtained: 1) there is a better agreement between the measured spectrum and the predicted one by the mathematical model; 2) there is no need to perform a background measurement in the suspending fluid without particles and/or the need to have a different section for the background measurement as in the prior-art.

Positioning of the transmitter and receiver transducers 20, 22 and 24, 26 respectively, relative to each other is controlled automatically by the computer 34 through position control device 27. Positioning of the transmitter and receiver transducers is also controlled automatically to provide good sensitivity and accuracy within the range of the particular attenuation level being measured. For example, if the attenuation at a particular point is very low, a greater distance between the transmitter and the receiver transducers would be preferred to give a higher attenuation reading. On the other hand, if the attenuation is too high and the signal at the receiver undetectable, the distance between transducers is automatically decreased down to a point where accurate readings of the attenuation can be obtained. This automatic feedback control of the spacings increases the signal-to-noise ratio considerably with the benefit of, again, achieving a better agreement between the measured spectrum and the predicted one by the mathematical model.

The attenuation spectrum for the sample suspension 12 is thus developed by a series of measurements at selected discrete frequencies within the selected frequency range. A typical attenuation spectrum can have about 40 or so measurement points distributed with an equal logarithmic spacing over a frequency range of from about 0.5 Mhz to about 100 Mhz, each at a selected frequency and each being taken at several (two or more) different spacings between the transmitter and receiver transducers to null out the effect of system constants as explained above. The entire process is conducted under the control of the computer 34 which is programmed in any suitable and well-known manner to carry out the prescribed steps in sequential fashion. A typical measured attenuation spectrum is presented in FIG. 2 which presents on a logarithmic scale the attenuation of an ultrasonic wave passing through a suspension of limestone in water, measured in dB/inch as a function of the frequency of the ultrasonic wave excitation, with the points between the measurement points being smoothed to present a continuous curve.

Figure 2:
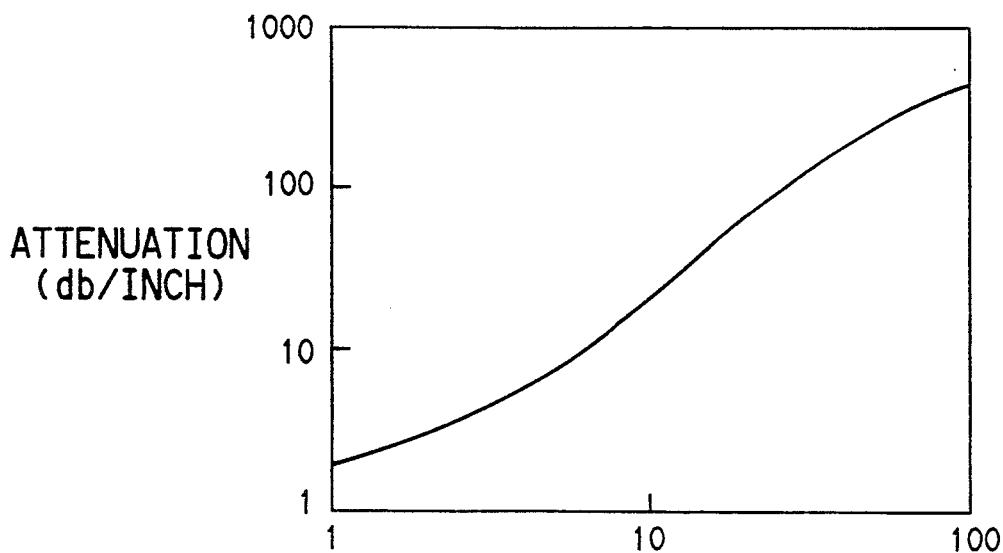
FIG. 2 is a plot of a typical attenuation spectrum for limestone in water.
Figure 3:
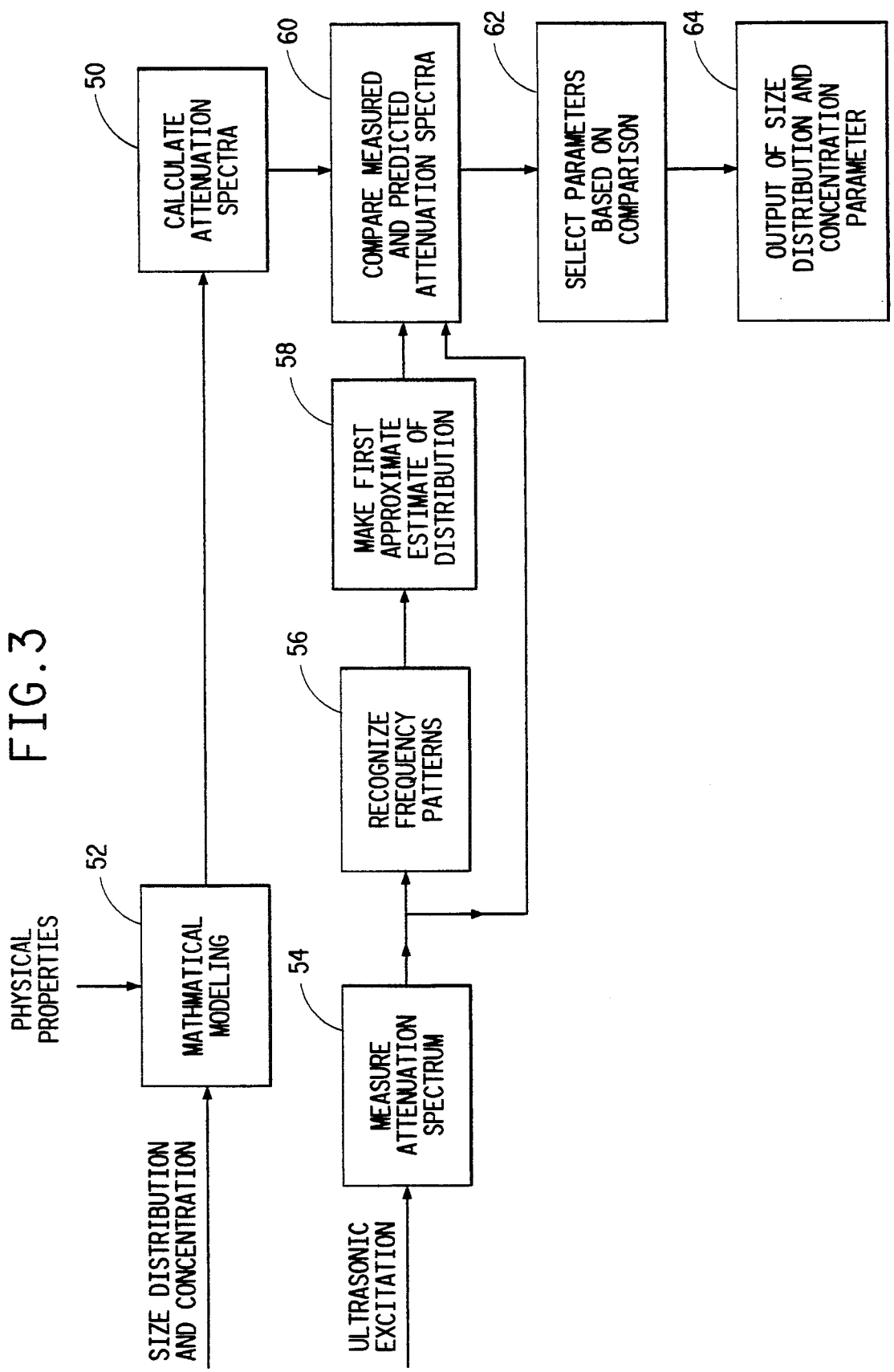
FIG. 3 is a functional block diagram for the method.

Referring now to FIG. 3, there is presented a block diagram showing in simplified form the basic methodology of the method of one embodiment of the present invention which provides for the derivation of initially unknown size distribution and concentration of particles in a suspension from the measured attenuation spectrum as exemplified in FIG. 2.

In the diagram of FIG. 3, block 50 represents the step of calculating a set of attenuation spectra for a selected wide range of particle size distributions and concentrations for ultrasonic waves at excitation frequencies over a range including those frequencies at which measurements are to be made. In one embodiment, the attenuation spectrum in the frequency range of from about 0.5 Mhz to about 100 Mhz is predicted for the size range 0.01 $\mu$m to 1,000 $\mu$m and the concentration range 0.0% to 70% by volume. These frequency and size ranges are discretized typically with much higher resolution than the frequency measurement points and number of size fractions in the size distribution to be determined. The concentration range can be covered continuously as needed due to the nature of the equations as will be explained.

The calculation of the attenuation spectra is based on mathematical modeling represented by block 52 which utilizes as its inputs the physical properties, either assumed or actual if known, of the particles and of the suspending medium, and of an assumed size distribution and concentration. The details of the mathematical modeling will be presented later.

The measurement of the attenuation spectrum of the sample in the manner already described is represented by block 54. The measured attenuation spectrum from block 54 is then inspected for known frequency patterns the computer can recognize as shown by block 56 so a first approximate estimate for the distribution can be obtained. This is represented in block 58. With this first estimate as a starting point, the measured attenuation spectrum from block 54 is then compared at block 60 with the matrix of calculated attenuation spectra from block 50 and a match is derived in accordance with mathematical matching formulae to be later described. When a match is determined in accordance to the selected formula, the original parameters of size distribution and concentration used to calculate the matching model are selected at block 62 as the matching parameters corresponding to the measured attenuation spectrum. The output of the system at 64 is then the size distribution and concentration based on the match between the calculated attenuation spectra and the measured attenuation spectrum of the test sample.

These calculations, as it will be later described, can be made rapidly in accordance with the requirements for on-line process control and utilizing a computer with only modest computational power.

A further description of the details of the above described steps of the method of the present invention will now be presented.

The parameters utilized to predict the attenuation spectrum are thermodymical, mechanical and transport properties of both phases (suspending and suspended media). Specifically, they are viscosity, shear rigidity, density, specific heat, thermal dilatability, intrinsic ultrasound attenuation and speed of sound.

The mathematical modeling starts by fundamentally describing the physical interaction between an ultrasonic plane wave and a single particle, then extending the mathematics to predict the interaction between the wave and a population of identical particles (monosize distribution), and finally, the model is completed by characterizing the interaction between the sound and a population of particles of a plurality of sizes (polysize distribution).

An ultrasonic wave of energy passing through a slurry results in changes to the wave and changes to both phases of the slurry. A particle presents a discontinuity to sound propagation (change in density, velocity, etc.) and the wave scatters. Particles move resulting in viscous-drag effects. Differences in temperature at the particle and the suspending medium cause heat flow absorbing energy from the wave. These effects are well known and can be characterized through fundamental equations based on the laws of conservation of mass, energy and momentum, and thermodynamical equations of state, and stress-strain relations for isotropic elastic solids. Using these known relationships, two field equations for each phase of the suspension or emulsion can be formulated as follows:

$$\frac{\partial^3 \xi}{\partial t^3} = \frac{-C^2_1 \beta}{\gamma} \nabla T + \frac{\mu}{\rho} \nabla^2 \dot{\xi} +$$

$$\nabla(\nabla \cdot \xi) \cdot \left[ C^2_1/\gamma + \frac{4\mu}{3\rho} \right]$$

[1]

-continued $$\frac{(\gamma - 1)}{\beta} \nabla \cdot \xi + T = \gamma \sigma \nabla^2 T \qquad [2]$$

Assuming sinusoidal steady state, the field equations may be transformed into Hemholtz wave equations for each of the media for the compressional, thermal and viscous potentials. These equations are:

$$\begin{aligned}(\nabla^2 + k^2_c)\phi_c &= o \\ (\nabla^2 + k^2_T)\phi_T &= o \\ (\nabla^2 + k^2_s)A &= o\end{aligned} \qquad [3]$$

$k_c$, $k_s$ and $k_T$ are the wave numbers for compressional, shear and thermal waves respectively. They are defined for each media as:

Fluid [4]

$$k_c = \frac{\omega}{c} + i\,\alpha_L$$

$$k_T = (1 + i)\left(\frac{\omega}{2\sigma}\right)^{\frac{1}{2}}$$

$$k_s = (1 - i)\left(\frac{\omega}{2\nu_s}\right)^{\frac{1}{2}}$$

Solid $$k_c = \frac{\omega}{c} - i\,\alpha_L$$

$$k_T = (1 + i)\left(\frac{\omega}{2\sigma}\right)^{\frac{1}{2}}$$

$$k_s = \left(\frac{\omega^2 \rho}{\mu}\right)^{\frac{1}{2}}$$

Assuming the sound wave is a compressional plane wave and the particle is spherical, the mathematical problem has spherical symmetry and a general solution to these equations can be obtained by expanding the potentials in terms of spherical Bessel and Hankel functions and Legendre polynomial—$j_n$, $h_n$ and $P_n(\cos(\theta))$—respectively. The following equations represent these solutions.

Suspending Medium $$\phi_i = \sum_{n=O}^{\infty} i^n(2n + 1)j_n(k_c r)P_n(\cos \theta) \qquad [5]$$

$$\phi_R = \sum_{n=O}^{\infty} i^n(2n + 1)A_n h_n(k_c r)P_n(\cos \theta)$$

$$\phi_T = \sum_{n=O}^{\infty} i^n(2n + 1)B_n h_n(k_T r)P_n(\cos \theta)$$

$$A = \sum_{n=O}^{\infty} i^n(2n + 1)C_n h_n(k_s r)P^1_n(\cos \theta)$$

Suspended Medium $$\phi'_c = \sum_{n=O}^{\infty} i^n(2n + 1)A'_n j_n(k'_c r)P_n(\cos \theta) \qquad [6]$$

$$\phi'_T = \sum_{n=O}^{\infty} i^n(2n - 1)B'_n j_n(k'_T r)P_n(\cos \theta)$$

$$A' = \sum_{n=O}^{\infty} i^n(2n + 1)C'_n j_n(k'_s r)P_n(\cos \theta)$$

In these expansions, $\phi_i$ represents the impinging wave potential, $\phi_R$ the reflected wave potential, $\phi_c$ the refracted wave potential, $A$ and $A'$ the nonvanishing component of the viscous wave potentials outside and inside the particle respectively, and $\phi_T$ and $\phi_T'$ the thermal potentials for suspending and suspended media respectively.

Boundary conditions are next assumed and applied to the above general solution to arrive at the specific solution. The boundary conditions are established by assuming continuity of the stress components, temperature, heat flow and velocity of the particle and suspending medium at the surface of the particle. Primed variables represent a condition of the particle, unprimed variables represent a condition of the suspending medium. The boundary conditions are expressed as:

$$v_r = v'_r;\ v_\theta = v'_\theta;\ T = T';\ \tau\frac{\partial T}{\partial r} = \tau'\frac{\partial T'}{\partial r}; \qquad [7]$$

$$P_{rr} = P'_{rr};\ P_{r\theta} = P'_{r\theta}$$

These boundary conditions are next expressed as a function of the potentials. Combining the wave equation solutions and the boundary conditions and taking advantage of the orthogonality property of spherical harmonics, results in six algebraic equations with complex arguments, one for each term of the series. The six coefficients $A_n$, $B_n$, $C_n$, $A'_n$, $B'_n$, $C_n'$ can be determined by solving these equations.

The next step is to generalize this mathematical formalism for a single particle to the case of a population of identical particles. It is known that for particle concentrations higher than about 10% to 15% by volume, the phenomenon of multiple-scattering of the wave can not be neglected. The mathematical modeling of multiple-scattering in the present invention employs the theory of Waterman & Truell (Journal of Mathematical Physics, Volume 2, Number 4, 1961) and its subsequent modifications by several authors.

By employing the statistical concept of a configurational average of the acoustical field over the ensemble of all possible spatial distribution of the scatterers (particles) developed by Foldy (Physics Review 67, Feb. 1 and 15, 1945), Waterman & Truell arrived at a fundamental mathematical relation between the propagation constants of the suspension and the suspending medium, valid for very high concentrations where multiple-scattering phenomena are dominant. The basic equation is:

$$\left[\frac{K}{k_c}\right]^2 = \left[1 + \frac{2\pi n_0[f(O)]}{k_c^2}\right]^2 - \left[\frac{2\pi n_0[f(\pi)]}{k_c^2}\right]^2 \qquad [8]$$

The most remarkable feature of this equation is that it represents the interaction between the sound wave and the whole population of suspended particles in terms of $[f(\theta)]$ which is the far acoustical field amplitude due to interaction of the wave and a single particle Then, for a population of identical particle of size d, the following equations hold:

$$[f(o)] = f(o, d) = \left(\frac{1}{ik_c}\right) \sum_{n=0}^{\infty} (2n - 1)A_n \quad [9]$$

$$[f(\pi)] = f(\pi, d) = \left(\frac{1}{ik_c}\right) \sum_{n=0}^{\infty} (-1)^n (2n + 1)A_n \quad [10]$$

The coefficients $\{A_n\}$ have already been calculated from the solution of the single particle problem.

Next, it is straightforward to calculate the attenuation of the wave since, by definition of the wave number, the excess attenuation $\alpha(\omega)$ (the total attenuation minus the one due to the suspending medium) is:

$$\alpha(\omega) = \alpha_{mp}(\omega,d) = Im\{K - k_c\} \quad [11]$$

$\alpha_{mp}(\omega,d)$ refers to the attenuation of the sound wave due to a population of monosize particles of side d at the frequency $\omega$.

For low concentrations the quadratic terms in $n_0[f(\theta)]$ can be neglected and, after some manipulation, the following well-known formula for the attenuation in dilute suspensions of monosize particles is obtained:

$$\alpha_{mp}(\omega,d) = \frac{3S_v}{2k_c^2(d/2)^3} \sum_{n=0}^{\infty} (2n + 1) \cdot Re\{A_n\} \quad [12]$$

It is clear from this equation that the attenuation is proportional to the particle concentration by volume $S_v$ as it was assumed in the prior art. This linear relation is obviously invalid in the general case (high concentration).

Finally, the interaction between the sound wave and a suspension or emulsion where a plurality of particles of different sizes exists must be mathematically described. As suggested by Waterman & Truell in the referenced article, the far acoustical field due to a polysize distribution, contemplating multiple-scattering phenomena between particles and the wave, can be expressed by superposition of the acoustical fields due to each one of the sizes in the population of particles. In mathematical symbolism, with D(d) being the density distribution function, it can be expressed:

$$[f(\theta)] = \int f(\omega,d)D(d)\, dd \quad [13]$$

It is worth noting that equation 13 involves the application of superposition on the acoustical field, the linearity of which is a basic assumption in ultrasonics. The prior-art, instead, applied superposition on the attenuation of the ultrasonic wave, as assumption known to be invalid for concentrations over 10% to 15% by volume.

Figure 4:
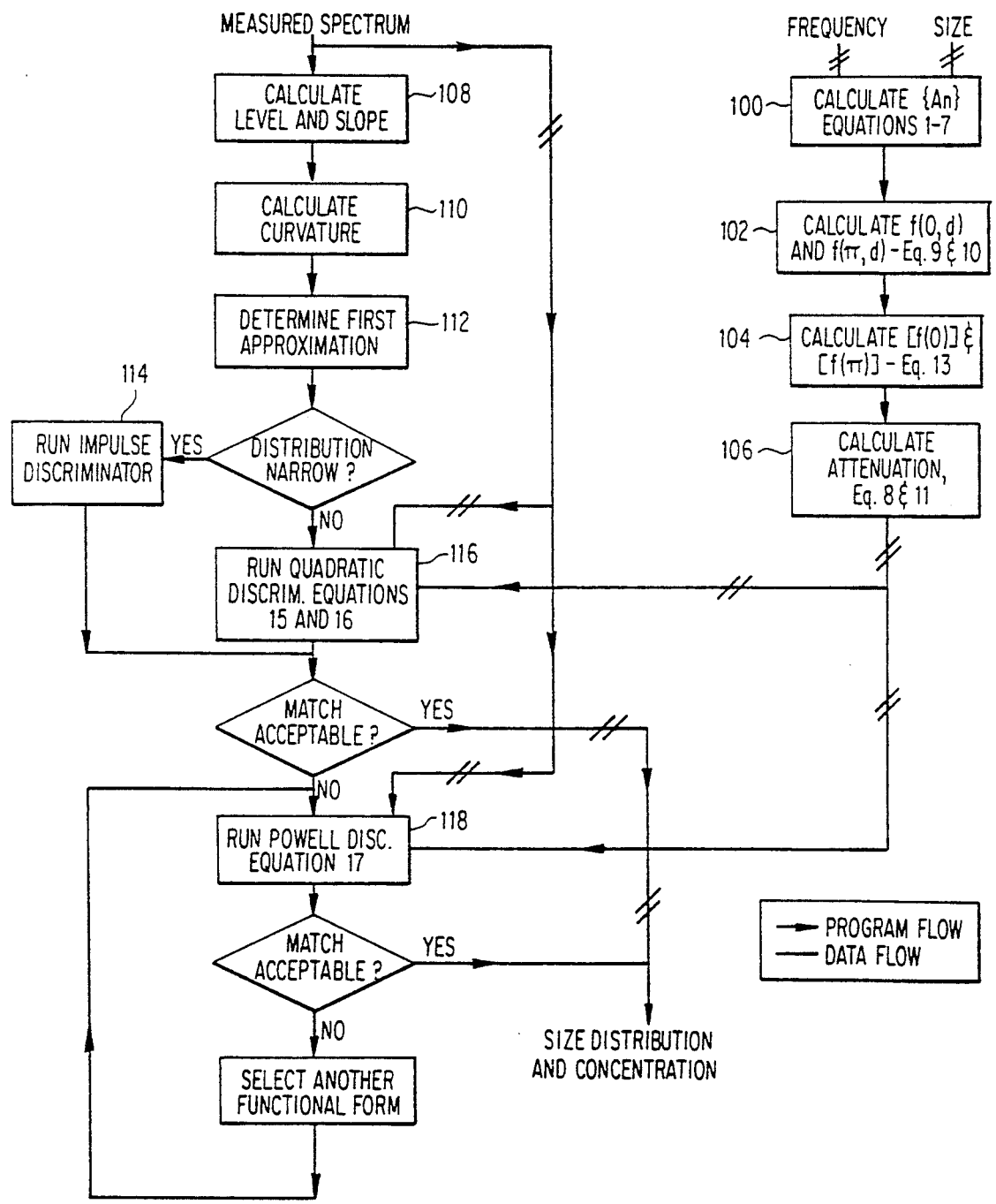
FIG. 4 is a general flow chart for the numerical computations.

The procedure to fully predict the attenuation spectrum in the general case of highly concentrated suspensions of polysize particle distributions has been completed and can be summarized as follows (refer to FIG. 4):

1) Coefficients $\{A_n\}$ are calculated for each frequency and size as explained through equations 1 to 7 (block 100);
2) f(O,d) and f($\pi$,d) are calculated using equations 9 and 10 (Block 102);
3) The acoustical fields [f(O)] & [f($\pi$)] due to the polysize distribution are calculated with equation 13 (block 104); and
4) The attenuation $\alpha(\omega)$ is calculated using equations 8 and 11 (block 106).

As a consistency check for this multiple-scattering model, when the quadratic term in $n_0[f(\theta)]$ is neglected (low concentration case) in equation 8 as before and, now, equation 13 for the polysize distribution is employed, the following formula for the attenuation of diluted suspensions is obtained:

$$\alpha(\omega) = \left(\int_0^\infty \alpha_p(\omega, d) \cdot D(d) \cdot dd\right) \cdot S_v \quad [14]$$

where $$\alpha_p(\omega, d) = \alpha_{mp}(\omega, d)/S_v$$

It is apparent from this formula that the attenuation due to a dilute polysize distribution is proportional to the particle concentration by volume and that, furthermore, it can be expressed as a linear combination of the size fractions $D(d)S_v dd$ in each size interval. It can also be interpreted as the total attenuation being expressed as the summation of the partial attenuations $\alpha_p(\omega,d)D(d)S_v dd$ due to the size fractions $D(d)S_v dd$ in each size interval. This fundamental relation, only valid when multiple-scattering phenomena are negligible at low concentration, justifies the linear system of equations assumed by Riebel in U.S. Pat. No. 4,706,509, even though Riebel did not disclose any physico-mathematical procedure to determine the attenuation coefficients $\alpha_p(\omega,d)$ (his coefficients $a_{ij}$).

In the general case, the complete procedure as set forth above is followed for the mathematical modeling and may be used to perform the functions illustrated in blocks 50 and 52 of FIG. 3 as described above. This mathematical model, based on the physics of ultrasound, makes it possible to calculate the attenuation spectra for any size distribution, concentration and chemical composition of the phases of the suspension unlike the prior art which relied on empirical relations of limited applicability.

In accordance with a preferred embodiment of the invention, the functions represented by the blocks 50 and 52 may be actually implemented in two or more different steps, with some of the steps being carried out off line in advance and the results stored in addressable matrix form in the memory of the computer 34. In such preferred embodiment, the far acoustical field amplitudes f(O,d) and f($\pi$,d) are calculated off-line with equations 1 to 7 and 9 and 10 for discrete values of size and frequency with high resolution. Resolution may be typically selected, for example, at 100 to 500 discrete frequencies logarithmically evenly spaced for the frequency range and about 20 to 50 discrete points per decade, also logarithmically evenly spaced, for the size range. These calculations are preferably performed off-line and stored in advance because they involve the solution of the wave equations for a wide range of measurement conditions. Such computations require a considerably amount of time of modest computing power, and can typically range into several hours or more of computing time, far too long for on-line operation.

The calculation of the acoustical field for a polysize distribution and the final computation of the attenuation spectrum are accomplished on-line with equations 13, 8 and 11 as the invention is measuring the test sample.

The invention then performs its function—to measure the particle size distribution and concentration—by, after measuring the attenuation spectrum, manipulating the mathematical model in the reverse direction so as to uniquely identify a size distribution and concentration which predicted spectrum matches the measured one. This is accomplished by means of a discriminator software to be next described in detail.

The discriminator part of the invention combines a set of numerical inversion techniques, each one of them with certain limitations and advantages, which gives the invention the capacity of measuring a vast variety of different suspensions in a wide range of size (0.01 μm to 1,000 μm) and concentration (0.1% to 70% by volume) with an accuracy and resolution which matches—and in some cases exceeds—the performance of other instruments based on different principles (like light-scattering and sedimentation). The numerical techniques are non-linear optimization tools which search for the minimum of an objective function (representing, in a suitable manner, the difference between the measured and predicted spectra), subject to constraints based on physical realities which limit the feasibility space for the solution search. The objective functions are non-linear and, therefore, the success of the numerical algorithm in finding the proper solution may be enhanced by selection of an initial point close enough to the actual solution so no other local minimum on the hypersurface of the objective function is mistakenly chosen. This is one of the reasons why any method or apparatus based on the prior art, assuming approximate linear models and employing standard inversion techniques, has only very limited applicability and the size range to be measured need to be known in advance.

Three major numerical inversion techniques have been designed and coded in computer 34. They can be described as a Quadratic Discriminator, a Powell Discriminator and the Impulse Discriminator. These techniques are employed by the invention separately or in sequence after a first approximation for the distribution, based on known frequency patterns of the measured spectrum, is obtained.

Figure 5:
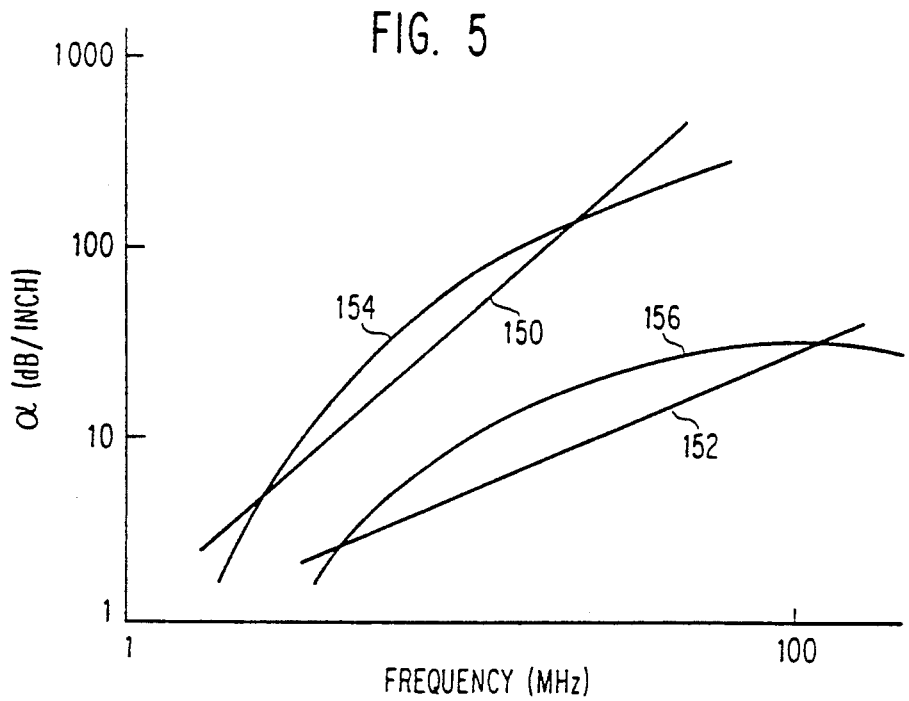
FIG. 5 shows typical frequency patterns for different size distributions.

The fundamental characteristics of the measured attenuation spectra which can be utilized in the first approximation to derive first estimates of the size distribution parameters are illustrated in FIG. 5 as an example. The attenuation spectra plotted are representative of suspensions of titanium dioxide in water and show attenuation as a function of frequency.

In general, the slope of the response curve increases as the distribution tends toward smaller particles. Thus response curves 150 and 154 are for smaller size particles and response curves 152 and 156 are for larger size particles. Also the curvature of the responses tends to increase (that is to deviate further from a straight line) as the size range of the particles becomes narrower. Thus, curves 150 and 152 indicate a broad size range distribution while curves 154 and 156 indicate a narrow size range distribution. These computations are represented in blocks 108 to 112 of FIG. 4. The Quadratic Discriminator is particularly desirable for concentrations below 15% by volume when equation 14 is valid. In equation 14, the left hand side $\alpha(\omega)$ is assumed known by measuring the attenuation of the wave as it passes through the suspension 12 in FIG. 1; $\alpha_p(\omega,d)$ is calculated with equation 12 and D(d) and $S_v$ are the unknown particle size distribution and concentration to be determined by the discriminator. This inversion problem is closely associated to the Fredholm Integral Problem of the First Kind which numerical solution has been studied by mathematicians for several decades. The main difficulty associated with this mathematical problem is its inherent instability: even round-off errors in $\alpha(\omega)$ or $\alpha_p(\omega,d)$ produce large variations on the unknown function large variations on the unknown function to an extent that most of its mathematical solutions have no physical meaning at all.

To solve this inversion problem by the Quadratic Discriminator, the integral equation is discretized in size and frequency giving rise to the following matrix equation:

$$\{\alpha_p \cdot \Delta F\} \cdot S_v = \alpha_m + \epsilon \quad [15]$$

where $\alpha_p$: is an M×N matrix with elements $\alpha_{pij}$ which are the quadrature coefficients with the measurement i in the size interval j.

$$\Delta F = (\Delta F_1, \Delta F_2, \ldots, \Delta F_N)^T \text{ with}$$

$$\Delta F_j = \int_{d_j}^{d_{j-1}} D(d) \cdot dd$$

$\alpha_m = (\alpha_1, \alpha_2, \ldots, \alpha_M)^T$ the vector of measurements.
$\epsilon = (\epsilon_1, \epsilon_2, \ldots, \epsilon_M)^T$ the error vector including modeling, quadrature and measurement errors.

Equation 15 is non-linear in the unknowns since it involves the products of the concentration $S_v$ with the size fractions $\Delta F_j$. Next step is to linearize the equation 15 around a point in the N+1 dimensional space $X = (\Delta F_1, \Delta F_2, \Delta F_N, S_v)$ transforming the non-linear equation 15 into a linear equation 16 as follows:

$$\alpha_p \cdot X = \alpha_m + \epsilon \quad [16]$$

It is worth noting that this linearization technique in no way restricts or limits the applicability of the quadratic discriminator or calls for the need of knowing in advance some information on the unknowns. It is simply a numerical technique to transform one problem into another. The non-linear problem is solved by iterative solutions of multiple linear problems which approximate closer and closer the non-linear one as the numerical algorithm approaches the exact solution.

In the same manner, any kind of independent restrictions to be imposed to the solution (smoothness of any kind, functional forms, etc.) can be easily implemented by adding new equations and possibly new variables to the basic matrix equation. The solution is then found by numerically solving the following quadratic estimation problem:

Minimize $$(\alpha \cdot X - \beta)^T \cdot W \cdot (\alpha \cdot X - \beta) \quad [17]$$

subject to the general linear constraints:
$A \cdot X < B; X_i \geq 0$

This is a very general formulation. $\alpha$ is a general matrix which can be partitioned as:

$$\begin{bmatrix} \alpha_p(M_x,1) | \alpha_s(M_x,2) | 0(M_x,N_F) \\ \alpha_c(M_{Cx},1) | 0(M_{Cx},2) | \alpha_f(M_{Cx},N_F) \end{bmatrix}$$

$\alpha_p$ is computed from equation 12; $\alpha_s$ includes a column corresponding to the solids concentration, $\alpha_c$ includes any constraints for stabilizing purposes and $\alpha_f$ can be employed to impose functional form restrictions on the unknown density function. $\beta$ is a general vector containing the actual measurements plus other components related to any constraints of convenience for each circumstance. This Quadratic Discriminator is the ultimate generalization of the quadratic programming approach.

The main limitation of such a quadratic discriminator as described above is that when the number of size fractions we want to recover increases slightly, the instability of the solution increases dramatically. It is very difficult to compensate even by increasing the frequency range and number of frequencies. Another important limitation of this estimator is that the fractions are fixed in number and position, and must cover the whole range of interest. Because of that, the quadrature error is significant and the measurement range can not be large—the larger the number of fractions the better the quadrature but the worse the stability of the solution.

To get around these limitations, a first inspection of the measured attenuation spectrum is made for known frequency patterns to determine an approximate estimate of the mean and spread of the distribution. With a good estimate of the region where the distribution is, the mathematical modeling program is used to calculate the quadrature matrix for a reduced number of size fractions (typically about eight) which are concentrated in the proper region of size and which therefore produce negligible quadrature error. The Quadratic Discriminator then estimates a size distribution. Once this estimated size distribution has passed all cross-validation checks, the program again requests from the mathematical modeling program the quadrature matrix (with a fewer number of size fractions, typically three) for each of the size fractions previously estimated, and, calling again the Quadratic Discriminator, delivers a new estimate of the distribution with more accuracy and resolution.

This nested discrimination procedure can be continued further to increase accuracy and resolution. Finally, cross-validation procedures will check each one of the partial as well as the whole distributions to be sure the combination of them is the optimal solution to all the available information on the problem, performing final adjustments and delivering the final estimated distribution.

Even though equation 16, on which the Quadratic Discriminator is based, is primarily valid for concentrations under 10% to 15%, in many cases this inversion algorithm is also useful for higher concentrations as it provides a first approximate solution to the non-linear general problem. These numerical computations are represented in block 116 of FIG. 4.

The Powell Discriminator is a second size distribution and concentration estimator. Instead of discretizing the unknown size distribution, a library of size distribution models (log-normal, Rosin-Rammler, etc.) is available. The following general nonlinear estimation problem is solved to find the best parameters for the unknown distribution as well as particle concentration:
Find $p_1,p_2 \ldots p_n, S_v$ which minimize:

$$(\text{ULTM}(p_1,p_2 \ldots p_n,S_v) - \beta)^T \cdot W \cdot (\text{ULTM}(p_1,p_2 \ldots p_n,S_v) - \beta) \quad [18]$$

Where the vector ULTM is the predicted attenuation spectrum for a number of well selected frequencies; $p_1,p_2 \ldots p_n$ are the parameters for the selected distribution model, $S_v$ is the concentration, $\beta$ the measurement vector of attenuations and W the weight diagonal matrix.

The advantage of this approach is that there is absolutely no assumption about the nature of the mathematical model for predicting the attenuation (linearity, discretization, etc.). In fact, this method calculates the vector ULTM by direct solution of the wave equations as described previously in the very general case where multiple-scattering can not be considered negligible. The name of this discriminator comes from the algorithm employed to solve this mathematical problem which is a Powell type optimization technique. In contrast, an assumption regarding the functional form of the distribution to be measured is made, and this may imply some limitation on the technique for handling general distributions. Nevertheless, the selection of the wrong distribution model can be detected by the discriminator as the match between measured and predicted spectra would not be acceptable. In such cases a different model is automatically selected. In a similar fashion multi-model particle size distributions can also be measured by the invention. These numerical computations are representations in block 118 of FIG. 4.

A typical sequence of numerical methods as performed by the invention when analyzing, for example, a suspension of glass particles in water is first to run the Quadratic Discriminator as a more general technique for deriving the region in which the solution resides and then to run the Powell Discriminator starting from the previous solution as the initial point. Typically, the solution from the Quadratic Discriminator is only an approximate one but good enough to feed the Powell Discriminator which provides a much more accurate and stable size distribution and concentration.

A third numerical method is the Impulse (monosize) Discriminator. When a first recognition of the measured spectrum indicates the distribution of particle sizes in the suspension is very narrow, the Quadratic and Powell Discriminator performance deteriorates substantially. In that case, the following impulse discrimination method determines the center of the impulse.

When the distribution is monosize, a single measured attenuation at a certain frequency can correspond to up to four different impulse centers (for a general distribution a single measurement correspond to an infinite number of distributions). However, due to the shift of the attenuation curves for different frequencies, if there were neither measurement nor modeling errors, two frequencies would be enough to discriminate the correct size from the four sizes possible for each frequency.

If the measurement error is known to be large, three (or more) frequencies are employed. Each inversion for each frequency will produce a maximum of four candidate particle sizes, giving a total of 12 (or more) different sizes. For a well selected frequency set, with no error, three (or more) of the 12 (or more) sizes should be the same, pinpointing the correct impulse center. In the real case, with error, three (or more) of them should cluster around the correct size. This numerical software is represented in block 114 of FIG. 4.

Characteristics such as those illustrated in FIG. 5 can be used to make a first approximation as already described and to select one or more of these stored discrimination algorithms for compared the calculated and measured attenuation spectra to accurately determine the size distribution and concentration. Other techniques in addition to those disclosed herein may also be used to compare the measured attenuation spectrum with the calculated attenuation spectra to arrive at an approximate acceptable match and thereby determine the unique values of the particle size distribution and concentration in the suspension.

Figure 6:
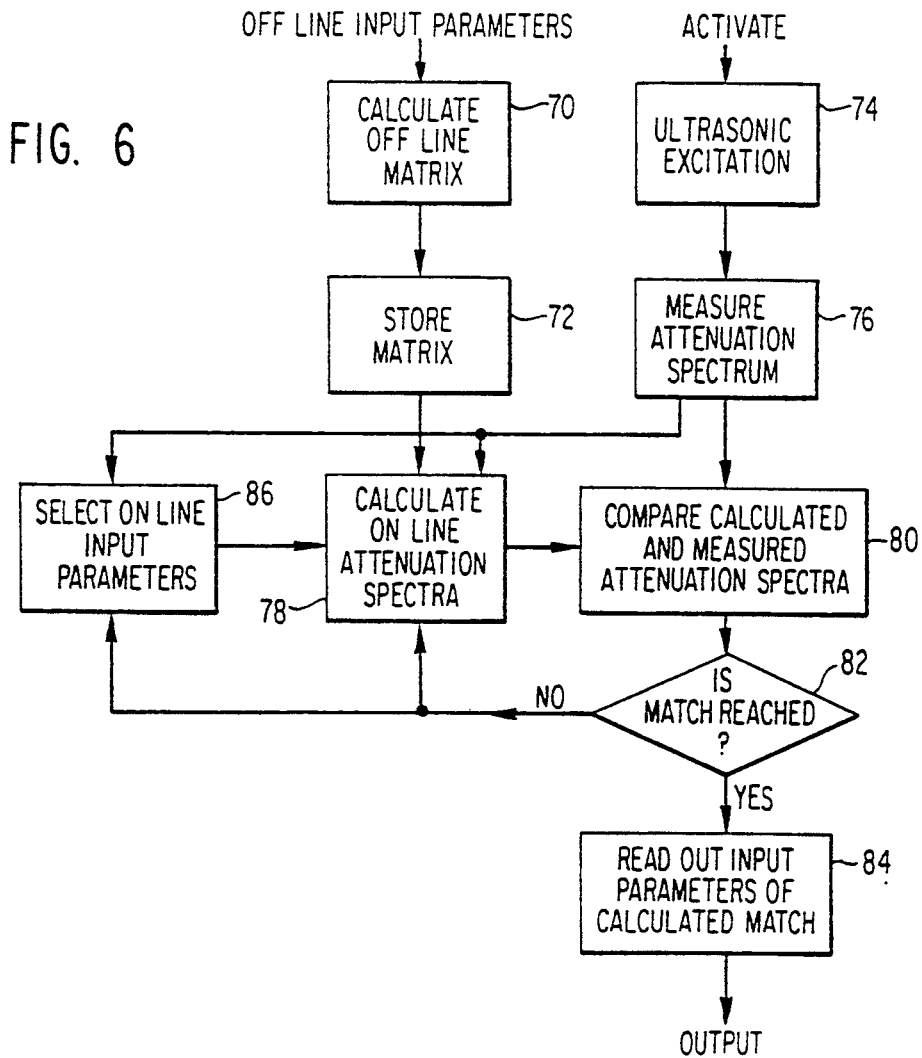
FIG. 6 is a streamlined general flow chart of the method.

A preferred embodiment which combines off-line calculation and storage in matrix addressable form of certain parameters and on-line calculation based on use of the stored matrix is shown in the flow chart of FIG. 6. Off-line calculation of the matrix is shown at step 70. As described above, in one preferred embodiment, this comprises the calculation of a set of attenuation spectra for selected monosize increments, a set in the range of about 100 to 500 monosize increments selected logarithmically evenly spaced over the range 0.01 $\mu$m to 1,000 $\mu$m, with an attenuation spectrum, extending over the selected frequency range, being calculated for each selected monosize of particles. The calculated attenuation spectra are stored at step 72 in the memory of computer 34, or in a memory addressable thereby, in the form of a matrix addressable through the parameters of size and frequency for each type of suspension. The stored matrix is thus made available to the computer 34 for use in the on-line calculations.

Measurement of the attenuation spectrum of the test sample is performed on-line as shown with the activation of the ultrasonic excitation of the sample as shown in step 74 and the measurement of the attenuation spectrum as shown in step 76. The measurement of the attenuation spectrum of the test sample is performed in the manner already described in detail above.

Sequential calculations of attenuation spectra are then performed as shown at step 78 and such calculated attenuation spectra are compared at step 80 with the measured attenuation spectrum until a match is reached based on a minimum difference between the calculated and measured spectra using the methodology as described above based on, for example, the minimum summation of the squares of the differences between measured and predicted attenuations at each frequency.

The calculated attenuation spectra are based on input parameters selected at step 86 which are preferably initially chosen as described above based on approximations derived from the measured attenuation spectrum at step 76. The measured attenuation spectrum derived from step 76 is thus used as an input to both the calculation process at step 78 and the initial parameter selection process of step 86 as shown in the diagram. The measured attenuation is also used in step 80 to compare the measured and calculated results. Sequential calculations are carried out from the initial set of assumed input parameters of size distribution and concentration in accordance with the stored discrimination techniques until a match is reached between the measured attenuation spectrum and a particular calculated attenuation spectrum. At that point, the program goes to step 84 and reads out the input parameters of size distribution and concentration which were used to calculate the matching calculated attenuation spectrum. These parameters are the output of the system and are unique solutions for the values of particle size distribution and concentration based on the match between the measured attenuation spectrum and the selected calculated attenuation spectrum.

The apparatus and method of the present invention provide for fast and accurate measurement of an initially unknown size distribution and concentration over a broad range. The present invention has been found to be particularly effective for very small particle sizes where mean size is less than about 5 to 10 microns and even more effective in the submicron region where mean particle size is less than 1 $\mu$m. The prior art methods, in addition to the other limitations mentioned above, have not been effective in the range of such small particle sizes and have been virtually ineffective in the sub-micron particle size range.

It is to be understood that mathematical techniques other than or in addition to those presented herein may be utilized to carry out the functions of the apparatus and to practice the method of the present invention and that the techniques disclosed herein have been presented for the purpose of making a full, clear and complete disclosure of the present invention and are not intended to limit in any way the scope thereof, which is defined in the appended claims.

Experimental results for limestone, glass and titanium dioxide will be presented next.

Figure 7:
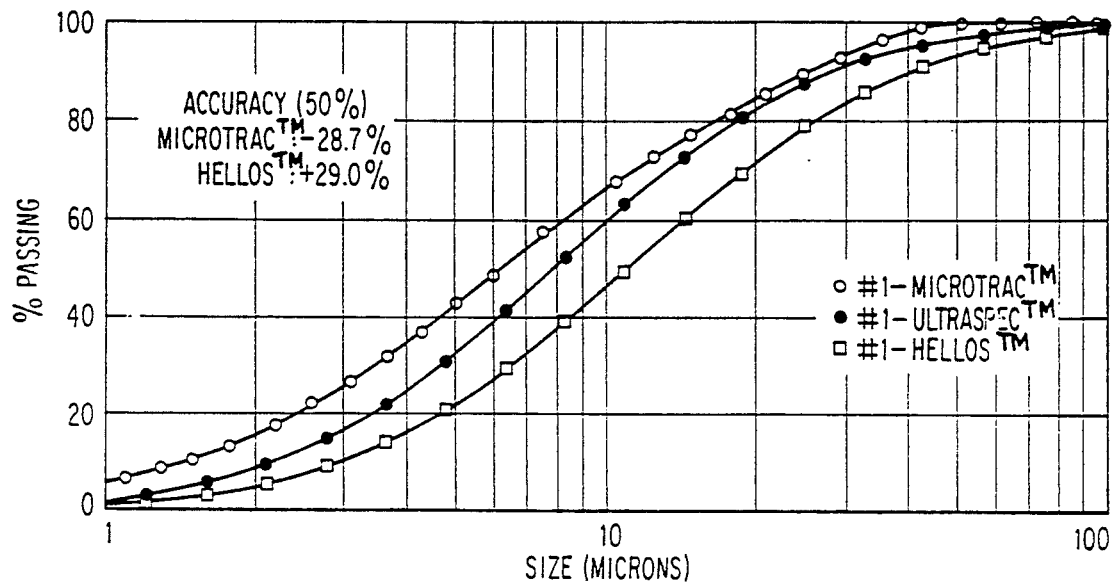
FIG. 7 compares experimental results for the present invention with other instruments based on the principle of light-scattering at about 10 microns.

FIG. 7 shows the size distribution delivered by the invention in comparison to the distributions delivered by two instruments available in the market, Microtrac TM and Helos TM, both based on the principle of light-scattering. The suspension is limestone in water at a concentration of 12% by volume. The invention determined a size distribution in between those delivered by the two instruments. The concentration delivered by the invention was within 1% of that determined by weighing the sample in the laboratory. Reproducibility of the measurements was about 1%.

Figure 8:
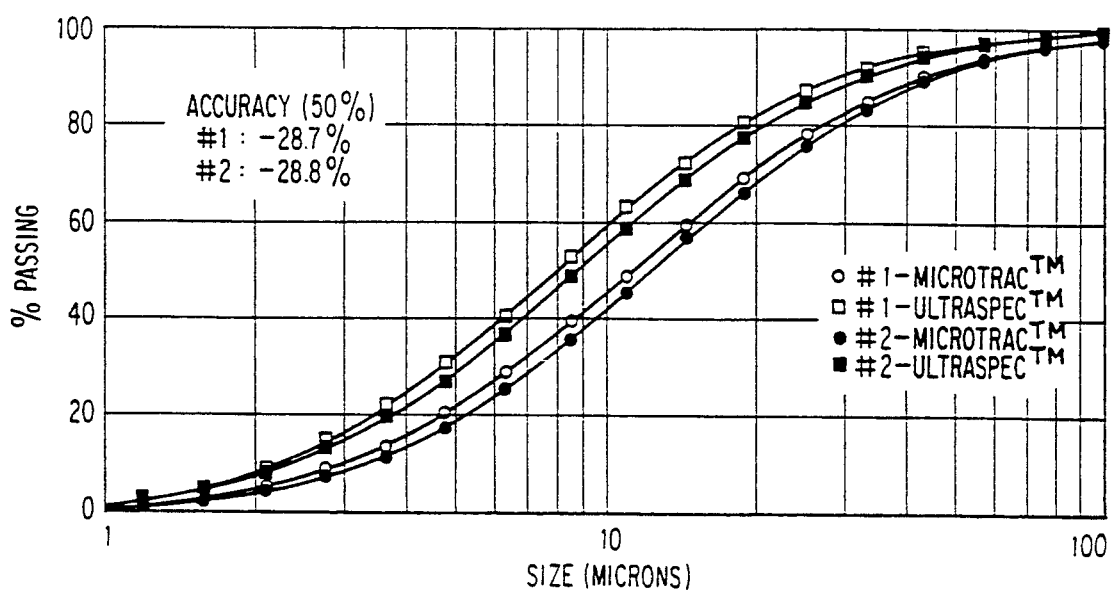
FIG. 8 demonstrates resolution of the present invention.

FIG. 7 demonstrates that resolution of the invention is better than 10% since it is capable of discriminating between two different samples differing each other on about 1 micron and having mean sizes of about 10 microns. The suspension was limestone in water at a concentration of 12% by volume. Accuracy is again contrasted with the Microtrac TM instrument based on light-scattering. The invention consistently delivered about 30% a finer distribution than the light-scattering instrument and it is known that the Microtrac TM instrument, in that size range, overestimates the particle size by about that amount (from evaluations of that instrument's performance with reference particles). FIG. 8, like FIG. 7, shows the size distribution delivered by the invention compared to the Microtrac TM instrument, using a suspension of limestone in water at a concentration of 12% by volume.

Figure 9:
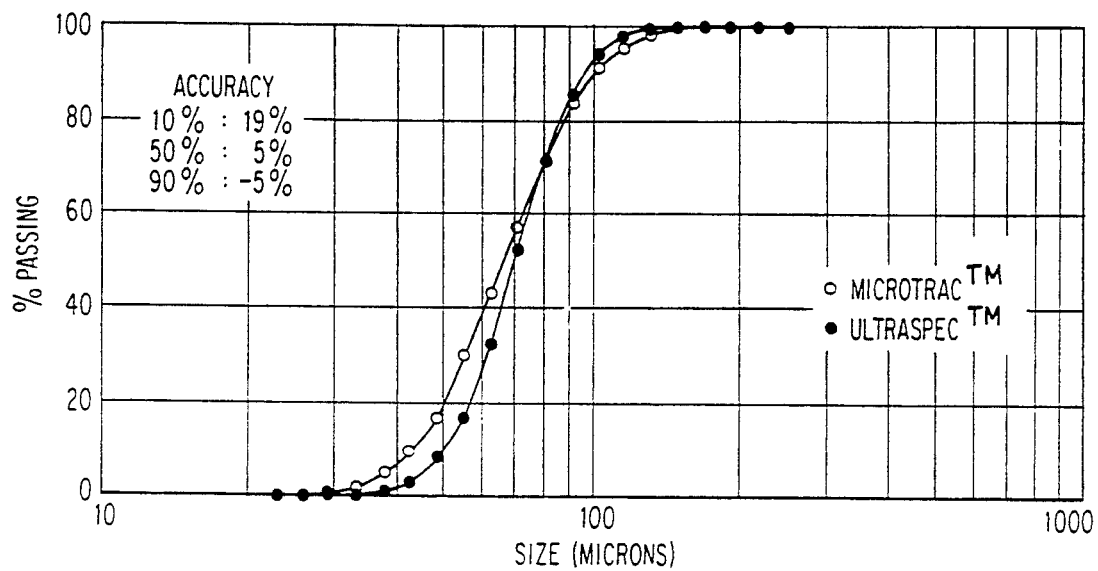
FIG. 9 compares results of the present invention with light-scattering at about 70 microns.

In FIG. 9 another comparison between the Microtrac TM instrument and the invention, this time for glass particles (i.e., glass shot MS-L, 5% by volume) of about 70 microns, is depicted. At this coarse size, both the light-scattering instrument and the ultrasonics-based present invention agreed within 5%.

The present invention is capable of measuring particle sizes smaller than a micron, and this capability was thoroughly tested with suspensions of titanium dioxide in water. This industrial application requires an on-line instrument capable of discriminating close distributions not only in terms of the mean sizes but also in terms of the spreads of the distributions. This ability of discriminating the tails of the distribution is paramount to control the quality of the product. The present invention has shown the required performance as it follows.

Figure 10:
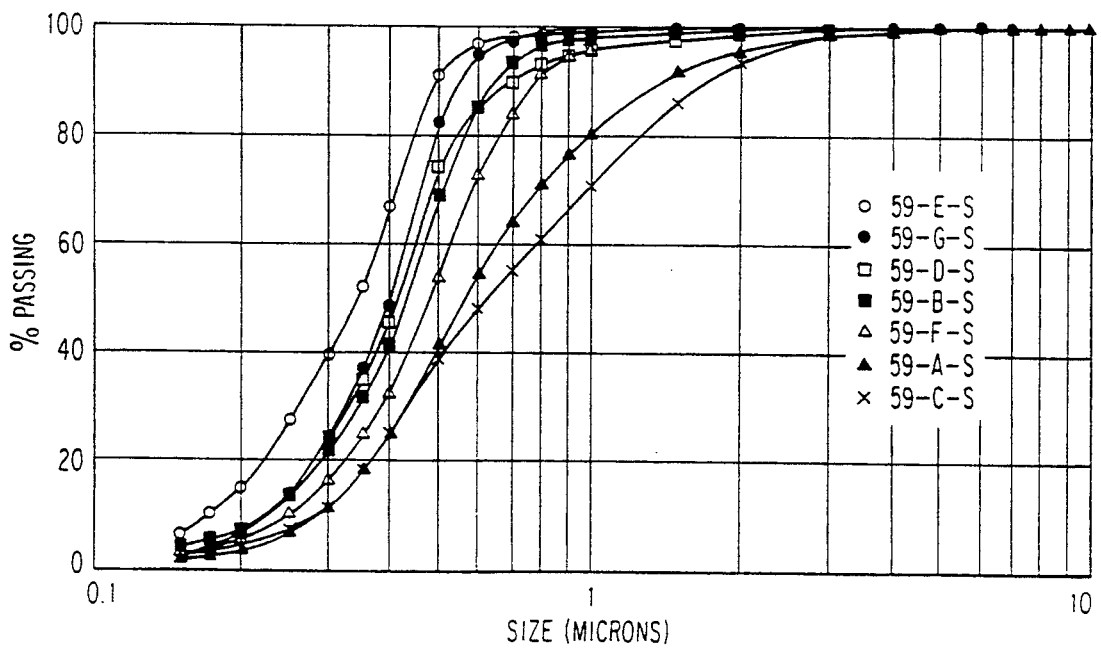
FIG. 10 depicts a series of titanium dioxide samples for testing of the present invention in the submicron range.

FIG. 10 plots the analysis results of seven samples of TiO2 as analyzed in the Sedigraph TM instrument based on the principle of sedimentation. The seven samples expand over the range of about 0.3 $\mu$m to about 0.6 $\mu$m for the mean size. Geometrical deviations of the series of samples expand from about 1.3 to about 2.3.

Figure 11:
FIG. 11 demonstrates discrimination capability of the invention in terms of the mean size and contrasted with the sedimentation principle.

FIG. 11 shows the order series for the geometric means and displays the Sedigraph TM results ordered according to the means from 0.34 $\mu$m (59-E) to 0.63 (59-C) in the first row; the row at the bottom depicts the order series established by the present invention. It can be seen that the present invention ordered the samples correctly; only G and D could be interchanged but Sedigraph TM results for them are very close and can easily be masked by the standard reproducibility of a sedimentation technique. It is clear that the present invention has a resolution at least as good as the well-established principle of sedimentation.

Figure 12:
FIG. 12 demonstrates discrimination performance of the invention in terms of the standard deviations and contrasted with the sedimentation principle.

Finally, in FIG. 12 the same samples are ordered in terms of the spreads of the distributions. FIG. 12 represents the order series for the geometric deviations. Again, the present invention discriminated the samples in the correct order. Only samples 59-E and 59-B were permuted but their respective deviations according to Sedigraph TM were very close (0.7%) and therefore both instrument show comparable discrimination powers.

The usefulness of the present invention for quality control of the titanium dioxide process is demonstrated by observing that samples 59-G and 59-D which were indistinguishable by their means, were easily discriminated by the present invention in terms of their spreads.

The good performance of the invention in the submicron range can be associated to the accuracy of the mathematical model for particle sizes much smaller than the wavelength corresponding to the maximum frequency of 100 Mhz, to the accuracy of the measured attenuation spectrum, and the possibility of measuring very low and very high attenuations on the same spectrum. Particles about 100 times smaller than the smallest transmitted wavelength are measurable with good resolution and accuracy.

The subject method and related analyzer can be used to measure particle size distribution and concentration of particles suspended in liquids, even in very concentrates slurries and dispersions, as previously mentioned. Therefore, it is useful in any process in which particles form, grow or remain suspended in liquids. It can be used for both organic or inorganic particles suspended in either organic or inorganic liquid or gas. The wide range of application, allow it to be used in a variety of processes such as crystallization, precipitation, emulsification, polymerization, grinding and attrition. It is useful for measuring changes in the dispersed state, such as agglomeration, aggregation and flocculation. It can be used to measure the size distribution and concentration in various streams from wet classification or separation processes, such as hydrocyclone, filter or centrifuge.

The method is applicable to both off-line or on-line operation. For example, it is useful to measure particle size distribution and concentration of hydraulically conveyed particles in pipes or channels. This on line capability enables it to be used for quality control or process control. In the latter mode, the measured signals pertaining to particle size distribution and concentration can be fed to a process control system. This can be in many forms, examples are: a conventional analog control system or microprocessor based instrumentation and digital computer network. These can involve feed-forward, supervisory, multivariable adaptive strategies as well as sophisticated digital logic. Such systems can be used to keep a manufacturing process close to its economic optimum.

| | LIST OF SYMBOLS |
|---|---|
| $\rho$ | Density |
| $\gamma$ | Ratio of specific heats. |
| $\tau$ | Thermal conductivity. |
| $\sigma = \gamma/\rho C_p$ | Thermal diffusivity. |
| $\beta$ | Thermal dilatability. |
| $\xi$ | Acoustical displacement. |
| $C_i$ | Sound speed for spherical compressional wave in elastic isotropic solid. |
| $C$ | Longitudinal sound velocity. |
| $\mu$ | Second Lame constant. |
| $T$ | Temperature. |
| $\eta_s$ | Shear viscosity. |
| $i$ | Imaginary unit. |
| $\nu_s$ | Kinematic viscosity. |
| $\alpha L$ | Intrinsic attenuation. |
| $\omega$ | Frequency. |
| $r, \theta$ | Spherical coordinates. |
| $v$ | Acoustical velocity. |
| $P$ | Stress tensor. |
| $n_o$ | Number of particles per unit volume. |
| Im | Imaginary part. |
| Re | Real part. |
| $K$ | Wave number of the suspension. |
| $k_c$ | Wave number of the suspending medium. |

I claim:

1. A method of determining the size distribution and concentration of particles in a suspension of particles in a suspending medium, comprising the steps of:
   directing ultrasonic waves through said suspension at selected discrete frequencies over a selected frequency range;
   measuring the attenuation of said ultrasonic waves passing through said suspension for each of said selected discrete frequencies to thereby obtain a measured attenuation spectrum for said suspension over said selected frequency range;
   calculating a set of attenuation spectra for the ultrasonic waves passing through said suspension over said selected frequency range;
   comparing said measured attenuation spectrum with said calculated attenuation spectra to derive an approximate match between at least one of said calculated spectra and said measured spectrum within a selected error range; and
   selecting the particle size distribution and concentration used to calculate said attenuation spectra to thereby derive a new set of values of particle size distribution and concentration corresponding to said measured attenuation spectrum.

2. A method as set forth in claim 1, wherein the step of calculating a set of attenuation spectra includes the step of calculating off-line a subset of attenuation spectra, storing the data of said calculated subset in a memory and subsequently using said stored data in the derivation of the values of particle size distribution and concentration corresponding to said measured attenuation spectrum.

3. A method as set forth in claim 2 wherein said calculated subset of attenuation spectra comprises a matrix of attenuation spectra for a plurality of monosize distribution of particle sizes.

4. A method as set forth in claim 3 wherein said matrix is addressable based on at least the parameters of particle size and frequency of ultrasonic excitation.

5. A method as set forth in claim 1, wherein the step of calculating a set of attenuation spectra includes making an initial section of a region of values of size distribution and concentration, said region being based on a first approximation derived from said measured attenuation spectrum, wherein the set of attenuation spectra is calculated within the region.

6. A method as set forth in claim 1, wherein the step of comparing said measured attenuation spectrum with said calculated attenuation spectra comprises deriving a first match between at least one of said calculated attenuation spectra and said measured attenuation spectrum and deriving a second match between at least another of said calculated attenuation spectra and said measured attenuation spectrum, the second match being more accurate than said first match.

7. A method as set forth in claim 1, wherein the step of measuring the attenuation is made at least at some of the selected discrete frequencies at a plurality of different transmission distances, and further wherein the measured attenuation is used to automatically control the transmission distances to eliminate the effects of noise and system parameters.

8. A method as set forth in claim 1 or 7 wherein the suspension contains particles with a means size of less than about 5 micrometers.

9. A method of set forth in claim 8 wherein the suspension contains particles with a means size less than about 1 micrometer.

10. A method of determining the size distribution and concentration of particles in a suspension of particles in a suspending medium, comprising the steps of:
    directing ultrasonic waves through said suspension at selected discrete frequencies over a selected frequency range and measuring the attenuation of said ultrasonic waves passing through said suspension for each of said selected discrete frequencies to thereby obtain a measured attenuation spectrum for said suspension over said selected frequency range;
    making a preliminary approximation of the particle size distribution based on said measured attenuation spectrum;
    calculating a set of attenuation spectra for the ultrasonic waves passing through the suspension over the selected frequency range;
    storing a plurality of algorithms and sequences of algorithms for calculating the size distribution and concentration from the measured attenuation spectrum, each of said algorithms being preferred for a predetermined set of conditions;
    selecting from said plurality of stored algorithms and sequence of algorithms at least one of the algorithms and the sequences of algorithms for a predetermined size distribution represented by said preliminary approximation; and
    utilizing said selected algorithm to determine the size distribution and concentration of said particles in said medium by matching, according to the at least one selected algorithms and sequences of algorithms, said calculated attenuation spectra with said measured attenuation spectrum.

11. An apparatus for determining the size distribution and concentration of particles in a suspension of particles in a suspending medium, comprising:
    means for directing ultrasonic waves through said suspension at selected discrete frequencies over a selected frequency range;
    means for measuring the attenuation of said ultrasonic wave passing through said suspension for each of said selected discrete frequencies to thereby obtain a measured attenuation spectrum for said suspension over said selected frequency;
    means for calculating a set of attenuation spectra for ultrasonic waves passing through said suspension over said selected frequency range, for numerically comparing said measured attenuation spectrum with said calculated spectra to derive an approximate match between at least one of said calculated spectra and said measured spectrum within a selected error range and for selecting the values of particle size distribution and concentration used to calculate said attenuation spectra to thereby derive a new set of values of particle size distribution and concentration corresponding to said measured attenuation spectrum.

12. Apparatus for determining the size distribution and concentration of particles in a suspending medium as set forth in claim 11 in which said means for measuring attenuation includes means for measuring the attenuation at at least some of said selected discrete frequencies over a plurality of different transmission distances.

13. An apparatus as set forth in claim 11, wherein said calculating, comparing and selecting means includes memory means having stored therein a set of pre-calculated attenuation spectra.

* * * * *